(12) United States Patent
Hicks et al.

(10) Patent No.: US 11,346,830 B2
(45) Date of Patent: May 31, 2022

(54) PREDICTIVE WATER CONDITION MONITORING

(71) Applicant: International Business Machines Corporation, Armonk, NY (US)

(72) Inventors: Andrew C. M. Hicks, Wappingers Falls, NY (US); Thomas William Conti, Poughkeepsie, NY (US); Diane Marie Stamboni, Poughkeepsie, NY (US); Christine D. Mikijanic, Monroe, NY (US); Christopher G. Brooker, New Paltz, NY (US); Andrew Evans, Fishkill, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 92 days.

(21) Appl. No.: 16/933,322

(22) Filed: Jul. 20, 2020

(65) Prior Publication Data

US 2022/0018824 A1   Jan. 20, 2022

(51) Int. Cl.
| | | |
|---|---|---|
| *G01N 33/18* | (2006.01) | |
| *G05B 23/02* | (2006.01) | |
| *G01W 1/10* | (2006.01) | |
| *G06N 20/00* | (2019.01) | |
| *G06N 5/04* | (2006.01) | |

(52) U.S. Cl.
CPC ............. *G01N 33/18* (2013.01); *G01W 1/10* (2013.01); *G05B 23/027* (2013.01); *G05B 23/0254* (2013.01); *G06N 5/04* (2013.01); *G06N 20/00* (2019.01)

(58) Field of Classification Search
CPC ..... G01N 33/18; G01W 1/10; G05B 23/0254; G05B 23/027; G06N 5/04; G06N 20/00
See application file for complete search history.

(56) References Cited

U.S. PATENT DOCUMENTS

| | | | |
|---|---|---|---|
| 3,661,262 A | 5/1972 | Sanders | |
| 4,626,992 A | 12/1986 | Greaves et al. | |
| 5,527,450 A | 6/1996 | Burrows | |
| 5,646,863 A * | 7/1997 | Morton | G01N 33/18 210/85 |
| 6,358,408 B1 | 3/2002 | Newman | |
| 6,753,186 B2 | 6/2004 | Moskoff | |

(Continued)

FOREIGN PATENT DOCUMENTS

| | | |
|---|---|---|
| CN | 203025177 U | 6/2013 |
| CN | 106815489 A | 6/2017 |
| TW | M450728 U1 | 4/2013 |

*Primary Examiner* — Mohammad K Islam
(74) *Attorney, Agent, or Firm* — Cantor Colburn LLP; Teddi Maranzano (57) ABSTRACT

Techniques for predictive water condition monitoring are described herein. An aspect includes a method that includes monitoring, by one or more processors, at least one water sensor to establish a baseline of a water condition model and monitoring one or more water conditions. A predicted water condition is determined based on the water condition model and the one or more water conditions. An alert is transmitted to one or more devices based on determining that the predicted water condition indicates a predicted contaminant level above a threshold.

19 Claims, 6 Drawing Sheets

(56) References Cited

U.S. PATENT DOCUMENTS

| | | | |
|---|---|---|---|
| 2002/0130069 A1* | 9/2002 | Moskoff | C02F 1/008 422/50 |
| 2017/0097647 A1* | 4/2017 | Lunani | G05B 19/04 |
| 2018/0305743 A1 | 10/2018 | Ghylin | |
| 2018/0327991 A1* | 11/2018 | Park | G06F 30/00 |
| 2021/0324649 A1* | 10/2021 | Revilla | C02F 1/008 |

* cited by examiner

PREDICTIVE WATER CONDITION MONITORING

BACKGROUND

The present invention generally relates to sensing and prediction systems, and more specifically, to predictive water condition monitoring.

Water quality can be impacted by a wide range of contaminants. Examples of contaminants include bacteria, waste matter, rust flakes, radiological matter, and chemical toxins of varying sizes. Water filters may be effective at capturing some contaminants; however, filters may not be fully effective. Further, some water distribution systems and fixtures may not be well-suited for installing filtration systems. Some water contamination problems may go unnoticed by people who consume the water, as the contaminants may not alter the appearance of the water or have an aroma detectable by humans.

SUMMARY

Embodiments of the present invention are directed to a method that includes monitoring, by one or more processors, at least one water sensor to establish a baseline of a water condition model and monitoring one or more water conditions. A predicted water condition is determined based on the water condition model and the one or more water conditions. An alert is transmitted to one or more devices based on determining that the predicted water condition indicates a predicted contaminant level above a threshold.

Other embodiments of the present invention implement features of the above-described method in computer systems and computer program products.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

The diagrams depicted herein are illustrative. There can be many variations to the diagrams or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

DETAILED DESCRIPTION

One or more embodiments of the present invention provide predictive water condition monitoring. Predictive water condition monitoring can be performed by a system that includes at least one water sensor to establish a baseline of a water condition model. In embodiments, a water sensor network including a plurality of water sensors at one or more known locations can be monitored to track variations in water conditions with respect to the one or more known locations. A larger set of water sensors can provide a wide area of coverage and increased opportunity for acquiring training data. A cognitive engine can perform machine learning to analyze patterns of changes in water conditions indicative of contamination and predict future water condition issues. As one example, trending of patterns shifting from a lower level of contamination to a higher level of contamination can trigger an alert to one or more devices of users likely to be adversely impacted. When applied over a large area, contamination patterns detected at a location can be used to trigger device notifications to other locations downstream or in an area of likely contaminant spread. Embodiments can operate at a combination of public and/or private water distribution locations. For example, water condition data can be collected from within structures/dwellings and/or from public distribution locations. Further, well water condition can be locally monitored, and data may be pooled with respect to one or more shared aquifers.

The machine learning aspects can apply any known techniques to detect data patterns and generate predictions. Integrating the machine learning aspects within a networked system can provide a more robust set of data to learn patterns and increase prediction accuracy. One or more water condition models can be trained using supervised, unsupervised, or partially-supervised training techniques. In a simple example, water conditions can be characterized based on electrical properties, such as conductivity. The water condition characterization does not need to be precise but can use fuzzy reasoning to make a drinkable/not-drinkable determination. Further, water condition characterization may be sub-partitioned into suitable-for-bathing-not-drinking and do-not-use conditions.

Water sensors can be attached in or on a pipe that is part of an established water line or installed at a junction between multiple pipes. The water sensors can be range from a simple pH checking device to a device that specifically detects physical blockages and debris. The water sensors may be packaged in modules that can be switched out when they reach a maximum life expectancy. Any sort of interface that can report water quality results can interface with the water sensors, such as wired or wireless communication interfaces. Data can be collected and saved in server, such as a web server, where the data may be processed and sent to a computing device for display/notification. The server can be equipped with a cognitive engine to analyze patterns in changing contamination and predict future issues.

In a household-based embodiment, the interface may include a battery backup and household electricity support for primary power. Multiple sensors can be installed at water junctions, in various rooms, near machinery such as water softeners and heaters, and at a main water source supply to a dwelling structure. The water sensors may output a binary response that can be directed to a device of a user. More complex forms may output a breakdown of toxins and contaminants in the water, along with tracking the patterns of contaminants over a specified period of time. The cognitive engine can utilize prior recorded entries in a database in order to construct a breakdown of past issues and predict what and when future issues may occur. Further, the water condition analysis support may generate hypotheses of possible sources of contaminants and possible treatments that would make the water usable. Information generated by the system can be reported to a water supplier as well as users of the water. As another example, municipal water supply monitoring and prediction can be performed for a public water supply. Water sensors and interfaces can be installed with a generator backup and primary power supplies or solar battery packs. A binary version can be reported to water users, whereas, a more complex breakdown of content can be sent to authorities monitoring the water supply.

Figure 1:
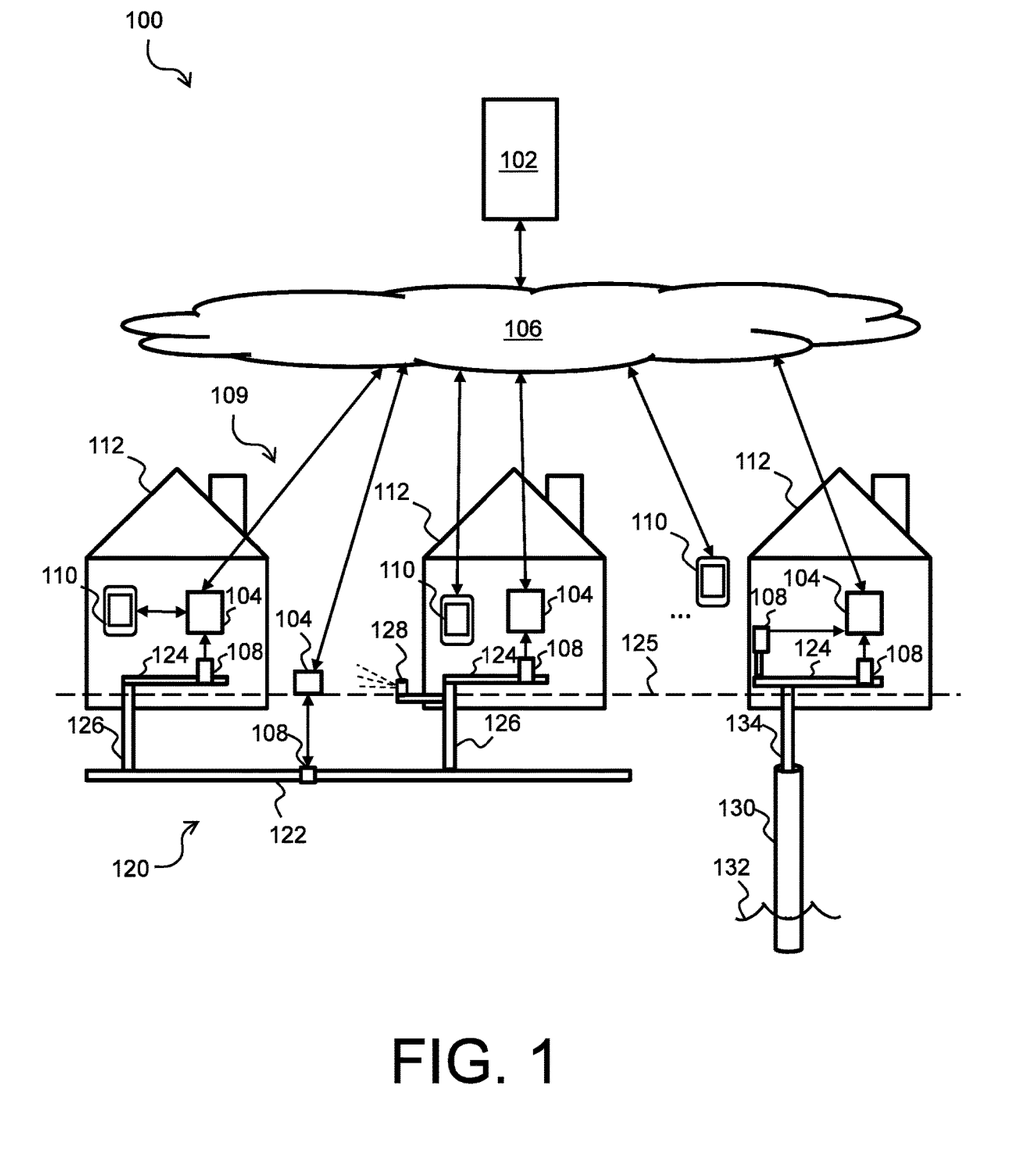
FIG. 1 illustrates a block diagram of components of a water distribution system in accordance with one or more embodiments of the present invention.

Turning now to a more detailed description of aspects of the invention, FIG. 1 depicts a system 100 in accordance with one or more embodiments of the present invention. System 100 can be implemented in conjunction with any appropriate computing device, such as computer system 600 of FIG. 6. The system 100 includes a server 102 and a plurality of interface systems 104 configured to communicate through a network 106. The interface systems 104 can interface with one or more water sensors 108 as part of a water sensor network 109. A plurality of devices 110 may be configured to communicate with the interface systems 104 and/or other systems reachable through the network 106, such as the server 102. As an example, the interface systems 104 can be configured to provide an excitation signal to one or more of the water sensors 108, perform analog-to-digital conversion of sensor data, and transmit the sensor data to the server 102. In some embodiments, the interface systems 104 can perform additional localized trending and detection of water conditions. As one example, a cognitive engine can be executed by the server 102 to learn water condition patterns and set one or more threshold criteria for defining a level of contamination. The threshold criteria can be flowed back to the interface systems 104 to enable rapid localized detection. Alternatively, contamination detection and predicted water condition can be determined by the server 102.

In some embodiments, one or more of the devices 110 can perform condition monitoring or condition prediction based on data provided from the interface systems 104 and/or from server 102. The devices 110 can be personal computers, laptops, tablet computers, smart phones, smart watches, wearable computing devices, appliance-based computing devices, or other such systems having a user interface. Further, the interface systems 104 and devices 110 can be integrated or further subdivided.

The water sensors 108 can be any type of water condition sensor and multiple types of water conditions can be detected within a same structure 112, across multiple structures 112, or elsewhere within a water distribution system 120. For example, water sensors 108 can be configured to detect water pH, alkalinity, hardness, chlorine level, particulate matter, salinity, organic matter, lead, iron, radon, and other such biological, chemical, mineral, and/or radioactive materials. The water sensors 108 can be within public distribution locations, such as main water lines 122 or in private distribution locations, such as plumbing lines 124 within structures 112. Placing water sensors 108 in close proximity to plumbing fixtures, such as faucets or other water dispensers can assist with detecting the condition of water as it is received by a user. Further, water sensors 108 may be installed in intermediate lines 126 between main water lines 122 and plumbing lines 124 to provide earlier detection of contaminants prior to reaching a plumbing fixture and/or to detect backflow contamination, for example, from a waste-water system or an irrigation system 128. Water sensors 108 may be configured to operate below or above ground 125.

The server 102 can also collect water condition data and determine predicted water conditions for private water systems, such as one or more wells 130 that access an aquifer 132 through a pipe and pump system 134. Private water system data may be localized by well location or grouped where the aquifer 132 is shared. Other types of well system data may also be tracked for use in a water condition model, such as well depth, pump size, well flow rate, service history, and the like.

It is to be understood that the block diagram of FIG. 1 is not intended to indicate that the system 100 is to include all of the components shown in FIG. 1. Rather, the system 100 can include any appropriate fewer or additional components not illustrated in FIG. 1 (e.g., clients, local datasets, additional memory components, embedded controllers, functional blocks, connections between functional blocks, modules, inputs, outputs, etc.). Further, the embodiments described herein with respect to system 100 may be implemented with any appropriate logic, wherein the logic, as referred to herein, can include any suitable hardware (e.g., a processor, an embedded controller, or an application specific integrated circuit, among others), software (e.g., an application, among others), firmware, or any suitable combination of hardware, software, and firmware, in various embodiments.

Figure 2:
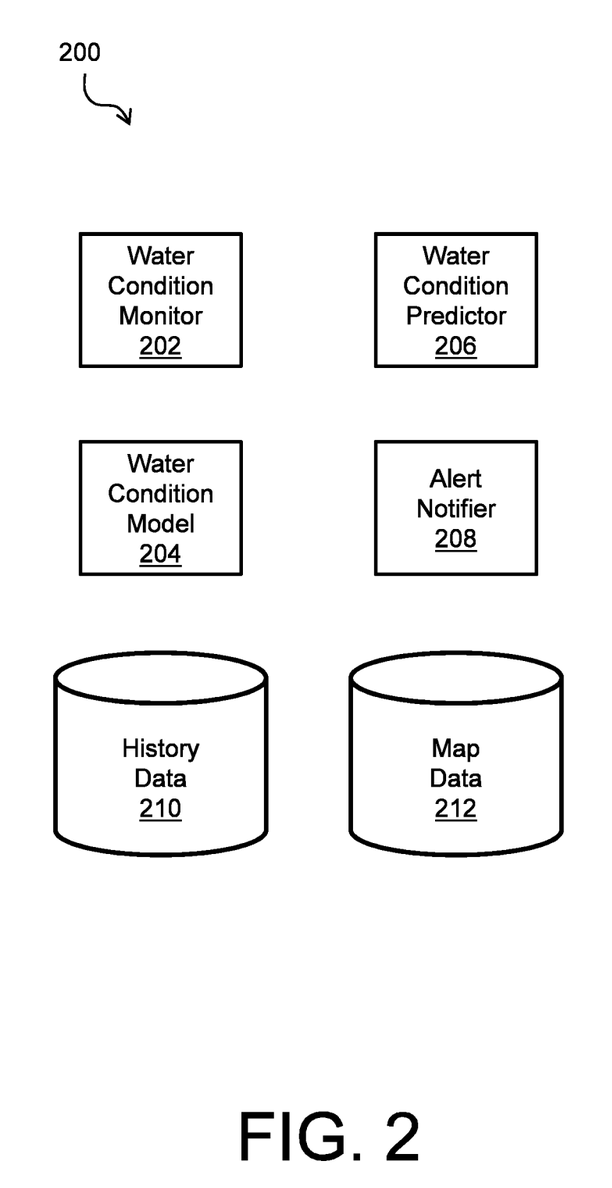
FIG. 2 illustrates a block diagram of components of a predictive water condition monitoring system in accordance with one or more embodiments of the present invention.

FIG. 2 depicts a predictive water condition monitoring system 200 in accordance with one or more embodiments of the present invention. Embodiments of system 200 can be implemented in, and are discussed in reference to, system 100 of FIG. 1. System 200 can include a water condition monitor 202, a water condition model 204, a water condition predictor 206, and an alert notifier 208. The water condition monitor 202 can receive sensor data from the water sensors 108 of FIG. 1. The water condition model 204 can learn how to interpret various inputs provided from the water condition monitor 202 and other inputs to characterize contamination relative to a baseline data set. Further, the water condition model 204 can generate derived parameters that relate to rates of change, patterns, water flow through the water system 120 of FIG. 1, parameters associated with wells 130 of FIG. 1, and/or aquifers 132 of FIG. 1. Outputs of the water condition monitor 202 and water condition model 204 can be tracked in history data 210.

The water condition predictor 206 can interface with the water condition monitor 202 and water condition model 204. The water condition predictor 206 can be a cognitive engine that learns patterns and uses inputs from other sensors or databases (not depicted) to assist in predicting future water contamination events. Water contamination can be predicted based on a gradual change in one or more characteristics of the water and may be linked to weather and/or environmental data. Further, where a rapid change in water condition is detected at a location within water distribution system 120 of FIG. 1, the water condition predictor 206 can predict a likely impact and propagation to other locations of the water distribution system 120 based on the water condition model 204 and map data 212. The map data 212 can include location information related to placement of the water sensors 108, water flow characteristics through sections of the water distribution system 120, and related data such as tidal basin locations, wetland locations, river and stream locations, storm drain and sewer location, and the like.

It is to be understood that the block diagram of FIG. 2 is not intended to indicate that the system 200 is to include all of the components shown in FIG. 2. Rather, the system 200 can include any appropriate fewer or additional components not illustrated in FIG. 2 (e.g., parameters, models, memory components, embedded controllers, functional blocks, connections between functional blocks, modules, inputs, outputs, etc.). Further, the embodiments described herein with respect to system 200 may be implemented with any appropriate logic, wherein the logic, as referred to herein, can include any suitable hardware (e.g., a processor, an embedded controller, or an application specific integrated circuit, among others), software (e.g., an application, among others), firmware, or any suitable combination of hardware, software, and firmware, in various embodiments. For instance, the system 200 may be implemented in server 102 of FIG. 1 or distributed between multiple devices, such as in a cloud computing environment.

Figure 3:
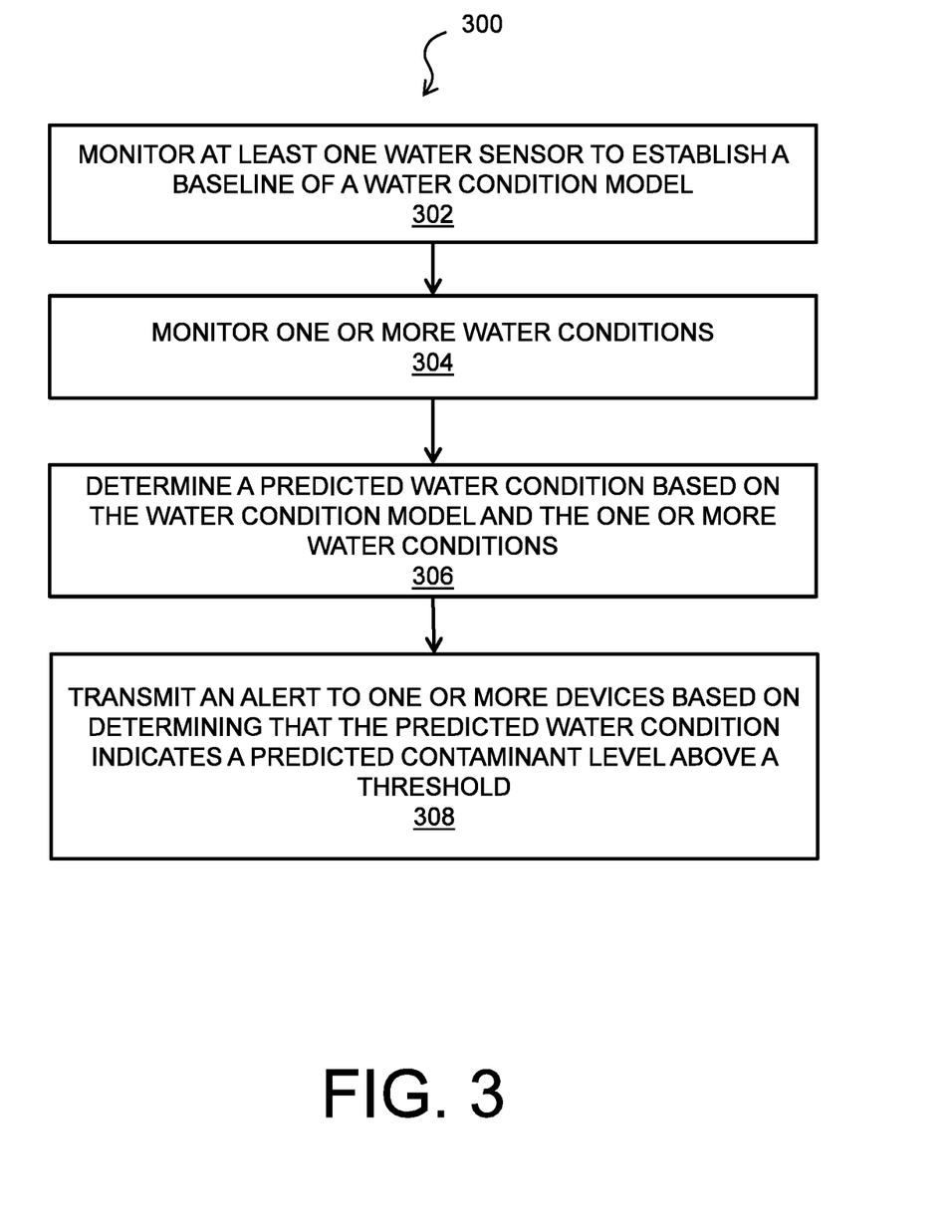
FIG. 3 illustrates a flow diagram of a process for implementing predictive water condition monitoring in accordance with one or more embodiments of the present invention.

Turning now to FIG. 3, a method 300 is generally shown in accordance with one or more embodiments of the present invention. Embodiments of method 300 as shown in FIG. 3 can be implemented by the system 100 shown in FIG. 1 and/or the system 200 of FIG. 2 and is described with respect to FIGS. 1 and 2.

At block 302, at least one water sensor 108 can be monitored to establish a baseline of a water condition model 204. At block 304, one or more water conditions can be monitored by the water condition monitor 202, where condition data may be derived from the water sensors 108 and/or other data sources. At block 306, a predicted water condition can be determined by the water condition predictor 206 based on the water condition model 204 and the one or more water conditions. At block 308, an alert can be transmitted by the alert notifier 208 to one or more devices 110 based on determining that the predicted water condition indicates a predicted contaminant level above a threshold. The alert notifier 208 can map notifications to devices 110, for example, based on the map data 212 or other data sources.

The monitoring can include interfacing with a water sensor network 109 including a plurality of water sensors 108 at one or more known locations. The water sensor network 109 can be distributed between a plurality of public and private water distribution locations. The water sensor network 109 can be interconnected using various network topologies. For example, the water sensor network 109 can be configured in a local and/or mesh network topology. Other network topologies may also be supported. Various security features, such as firewalls, may be incorporated between public and private portions of the water sensor network 109. Further, the water sensor network 109 can be associated with one or more wells 130 accessing an aquifer 132. Variations in the one or more water conditions can be tracked with respect to the one or more known locations. A probable location of introduction of a contaminant can be identified based on a rate of change of the one or more water conditions relative to the known locations of the water sensors 108. A notification can be generated of the probable location and the one or more water conditions. Machine learning can be applied to train the water condition model 204 to dynamically determine one or more characteristics associated with the one or more water conditions. Supplemental data can be accessed including one or more of a weather data source and an environmental data source. Machine learning can be applied to train the water condition model 204 based on one or more correlations between the one or more water conditions and the supplemental data. Forecast data can be accessed including one or more of weather forecast data and environmental forecast data. The water conditions can be predicted based on the water condition model 204 and the forecast data.

The process flow diagram of FIG. 3 is not intended to indicate that the operations of the method 300 are to be executed in any particular order, or that all of the operations of the method 300 are to be included in every case. Additionally, the method 300 can include any suitable number of additional operations.

In some aspects of the invention, the method 300 shown in FIG. 3 and the systems 100 and 200 shown in FIG. 1 and FIG. 2 can be implemented in a cloud computing system of the type described in the following paragraphs.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 4:
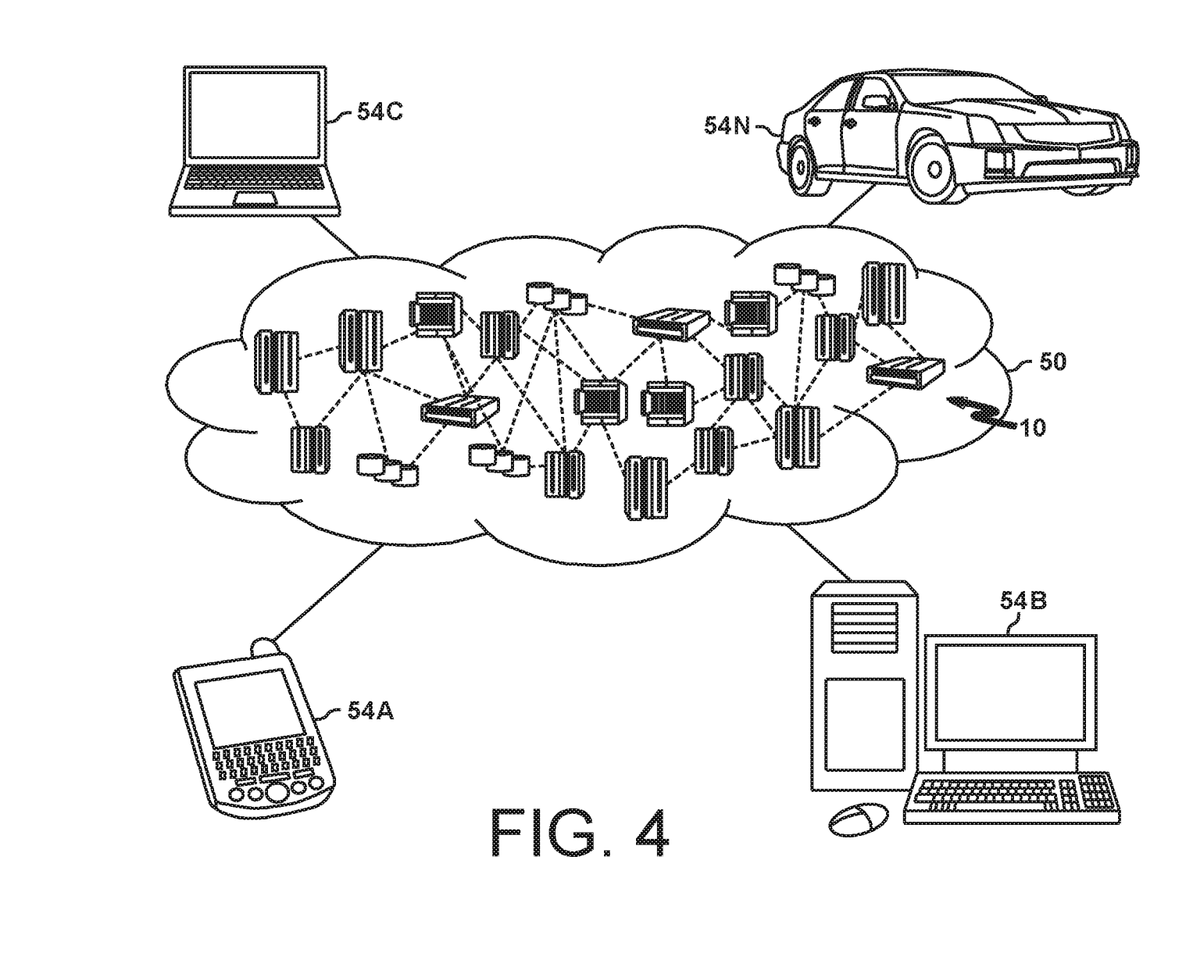
FIG. 4 depicts a cloud computing environment according to one or more embodiments of the present invention.

Referring now to FIG. 4, illustrative cloud computing environment 50 is depicted. As shown, cloud computing environment 50 includes one or more cloud computing nodes 49 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 10 and cloud computing environment 50 can communicate with any type of computerized device over any type of network and/or network addressable connection (e.g., using a web browser).

Figure 5:
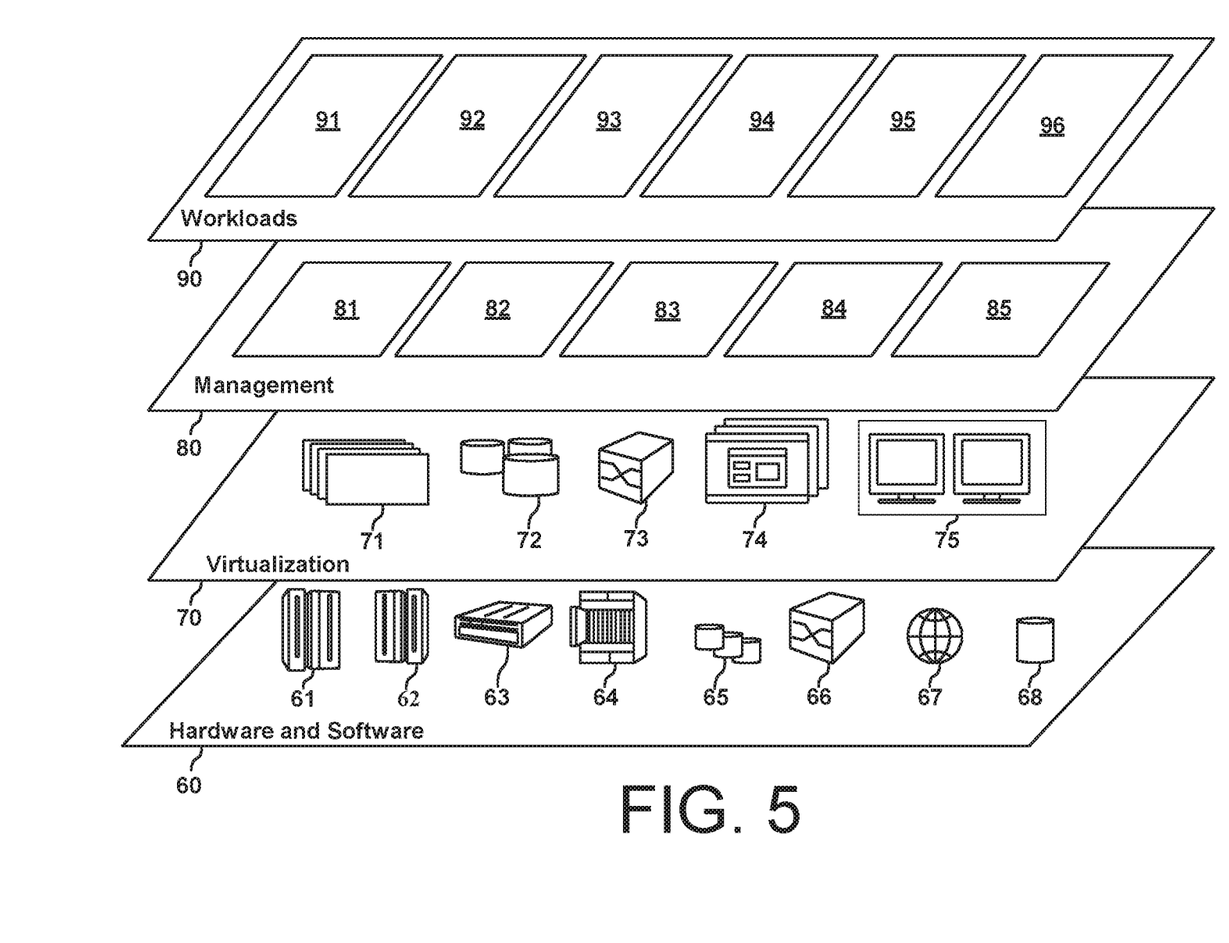
FIG. 5 depicts abstraction model layers according to one or more embodiments of the present invention.

Referring now to FIG. 5, a set of functional abstraction layers provided by cloud computing environment 50 (FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and predictive water condition monitoring system 96. The predictive water condition monitoring system 96 can include any of the components of system 200 of FIG. 2 and/or additional components.

Figure 6:
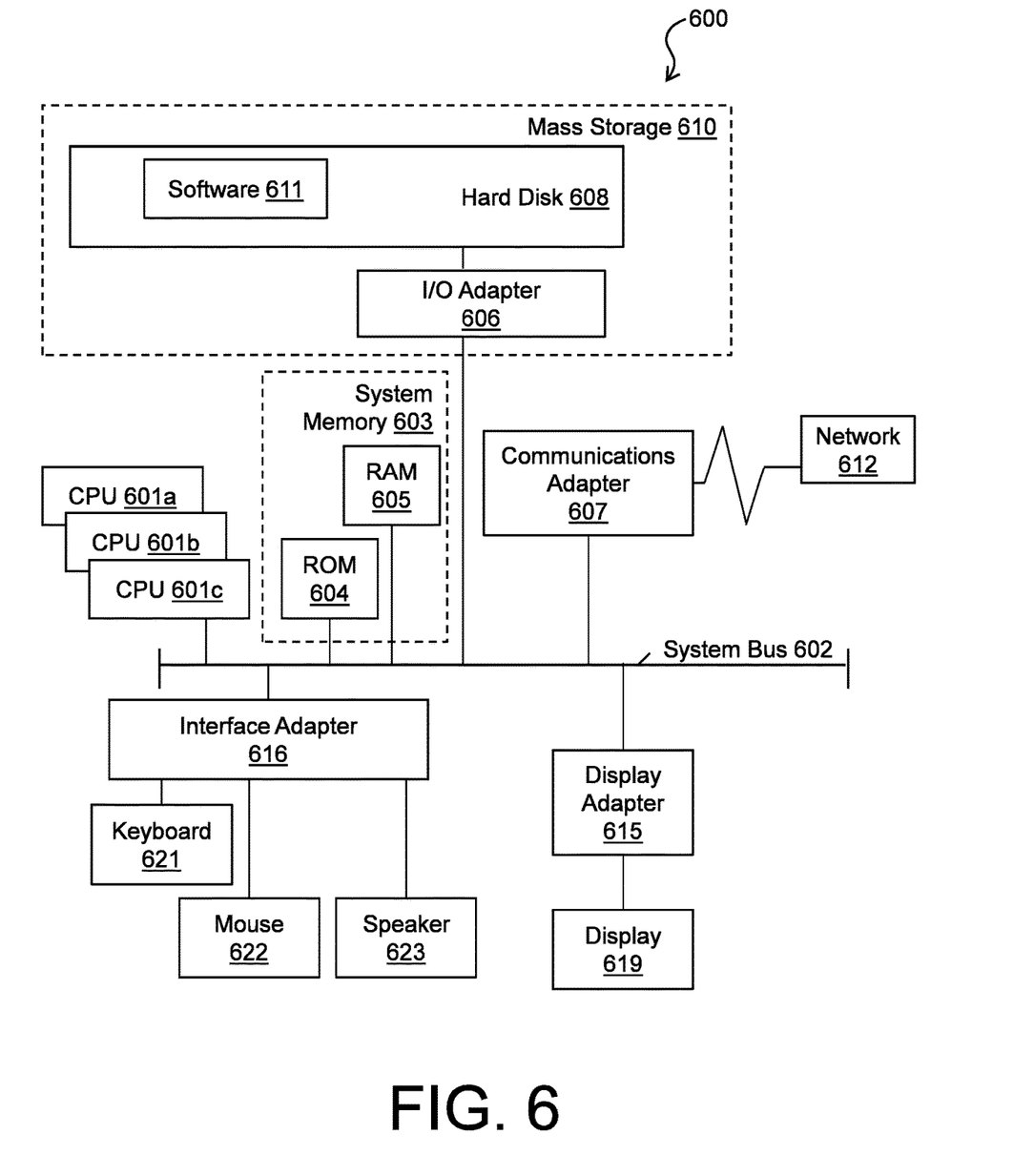
FIG. 6 is a block diagram of a computer system according to one or more embodiments of the present invention.

Turning now to FIG. 6, a computer system 600 is generally shown in accordance with an embodiment. The computer system 600 can be an electronic, computer framework comprising and/or employing any number and combination of computing devices and networks utilizing various communication technologies, as described herein. The computer system 600 can be easily scalable, extensible, and modular, with the ability to change to different services or reconfigure some features independently of others. The computer system 600 may be, for example, a server, desktop computer, laptop computer, tablet computer, or smartphone. In some examples, computer system 600 may be a cloud computing node. Computer system 600 may be described in the general context of computer system executable instructions, such as program modules, being executed by a computer system. Generally, program modules may include routines, programs, objects, components, logic, data structures, and so on that perform particular tasks or implement particular abstract data types. Computer system 600 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 6, the computer system 600 has one or more central processing units (CPU(s)) 601a, 601b, 601c, etc. (collectively or generically referred to as processor(s) 601). The processors 601 can be a single-core processor, multi-core processor, computing cluster, or any number of other configurations. The processors 601, also referred to as processing circuits, are coupled via a system bus 602 to a system memory 603 and various other components. The system memory 603 can include a read only memory (ROM) 604 and a random access memory (RAM) 605. The ROM 604 is coupled to the system bus 602 and may include a basic input/output system (BIOS), which controls certain basic functions of the computer system 600. The RAM is read-write memory coupled to the system bus 602 for use by the processors 601. The system memory 603 provides temporary memory space for operations of said instructions during operation. The system memory 603 can include random access memory (RAM), read only memory, flash memory, or any other suitable memory systems.

The computer system 600 comprises an input/output (I/O) adapter 606 and a communications adapter 607 coupled to the system bus 602. The I/O adapter 606 may be a small computer system interface (SCSI) adapter that communicates with a hard disk 608 and/or any other similar component. The I/O adapter 606 and the hard disk 608 are collectively referred to herein as a mass storage 610.

Software 611 for execution on the computer system 600 may be stored in the mass storage 610. The mass storage 610 is an example of a tangible storage medium readable by the processors 601, where the software 611 is stored as instructions for execution by the processors 601 to cause the computer system 600 to operate, such as is described herein below with respect to the various Figures. Examples of computer program product and the execution of such instruction is discussed herein in more detail. The communications adapter 607 interconnects the system bus 602 with a network 612, which may be an outside network, enabling the computer system 600 to communicate with other such systems. In one embodiment, a portion of the system memory 603 and the mass storage 610 collectively store an operating system, which may be any appropriate operating system, such as the z/OS or AIX operating system from IBM Corporation, to coordinate the functions of the various components shown in FIG. 6.

Additional input/output devices are shown as connected to the system bus 602 via a display adapter 615 and an interface adapter 616 and. In one embodiment, the adapters 606, 607, 615, and 616 may be connected to one or more I/O buses that are connected to the system bus 602 via an intermediate bus bridge (not shown). A display 619 (e.g., a screen or a display monitor) is connected to the system bus 602 by a display adapter 615, which may include a graphics controller to improve the performance of graphics intensive applications and a video controller. A keyboard 621, a mouse 622, a speaker 623, etc. can be interconnected to the system bus 602 via the interface adapter 616, which may include, for example, a Super I/O chip integrating multiple device adapters into a single integrated circuit. Suitable I/O buses for connecting peripheral devices such as hard disk controllers, network adapters, and graphics adapters typically include common protocols, such as the Peripheral Component Interconnect (PCI). Thus, as configured in FIG. 6, the computer system 600 includes processing capability in the form of the processors 601, and, storage capability including the system memory 603 and the mass storage 610, input means such as the keyboard 621 and the mouse 622, and output capability including the speaker 623 and the display 619.

In some embodiments, the communications adapter 607 can transmit data using any suitable interface or protocol, such as the Internet small computer system interface, among others. The network 612 may be a cellular network, a radio network, a wide area network (WAN), a local area network (LAN), or the Internet, among others. An external computing device may connect to the computer system 600 through the network 612. In some examples, an external computing device may be an external webserver or a cloud computing node.

It is to be understood that the block diagram of FIG. 6 is not intended to indicate that the computer system 600 is to include all of the components shown in FIG. 6. Rather, the computer system 600 can include any appropriate fewer or additional components not illustrated in FIG. 6 (e.g., additional memory components, embedded controllers, modules, additional network interfaces, etc.). Further, the embodiments described herein with respect to computer system 600 may be implemented with any appropriate logic, wherein the logic, as referred to herein, can include any suitable hardware (e.g., a processor, an embedded controller, or an application specific integrated circuit, among others), software (e.g., an application, among others), firmware, or any suitable combination of hardware, software, and firmware, in various embodiments.

As previously described, any of the server 102, interface systems 104, devices 110, and/or other components used to support systems 100, 200 of FIGS. 1 and 2 may include components of the computer system 600. Various user interfaces and appliances can use or embed embodiments of the computer system 600, such as a smart refrigerator, water dispenser, ice maker, coffee maker, or other such appliance.

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

One or more of the methods described herein can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

In some embodiments, various functions or acts can take place at a given location and/or in connection with the operation of one or more apparatuses or systems. In some embodiments, a portion of a given function or act can be performed at a first device or location, and the remainder of the function or act can be performed at one or more additional devices or locations.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The present disclosure has been presented for purposes of illustration and description, but is not intended to be exhaustive or limited to the form disclosed. Many modifications and variations will be apparent to those of ordinary skill in the art without departing from the scope and spirit of the disclosure. The embodiments were chosen and described in order to best explain the principles of the disclosure and the practical application, and to enable others of ordinary skill in the art to understand the disclosure for various embodiments with various modifications as are suited to the particular use contemplated.

The diagrams depicted herein are illustrative. There can be many variations to the diagram or the steps (or operations) described therein without departing from the spirit of the disclosure. For instance, the actions can be performed in a differing order or actions can be added, deleted or modified. Also, the term "coupled" describes having a signal path between two elements and does not imply a direct connection between the elements with no intervening elements/connections therebetween. All of these variations are considered a part of the present disclosure.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A method comprising:
monitoring, by one or more processors, at least one water sensor to establish a baseline of a water condition model;
monitoring one or more water conditions;
accessing supplemental data comprising one or more of a weather data source and an environmental data source;
applying machine learning to train the water condition model based on one or more correlations between the one or more water conditions and the supplemental data;
determining a predicted water condition based on the water condition model and the one or more water conditions; and
transmitting an alert to one or more devices based on determining that the predicted water condition indicates a predicted contaminant level above a threshold.

2. The method of claim 1, further comprising:
monitoring a water sensor network comprising a plurality of water sensors at one or more known locations; and
tracking variations in the one or more water conditions with respect to the one or more known locations.

3. The method of claim 2, wherein the water sensor network is distributed between a plurality of public and private water distribution locations.

4. The method of claim 2, wherein the water sensor network is associated with one or more wells accessing an aquifer.

5. The method of claim 2, further comprising:
identifying a probable location of introduction of a contaminant based on a rate of change of the one or more water conditions relative to the known locations of the water sensors; and
generating a notification of the probable location and the one or more water conditions.

6. The method of claim 1, further comprising:
applying machine learning to train the water condition model to dynamically determine one or more characteristics associated with the one or more water conditions.

7. The method of claim 1, further comprising:
accessing forecast data comprising one or more of weather forecast data and environmental forecast data; and
predicting the water condition based on the water condition model and the forecast data.

8. A system comprising:
a memory having computer readable instructions; and
one or more processors for executing the computer readable instructions, the computer readable instructions controlling the one or more processors to perform operations comprising:
monitoring at least one water sensor to establish a baseline of a water condition model;
monitoring one or more water conditions;
accessing supplemental data comprising one or more of a weather data source and an environmental data source;
applying machine learning to train the water condition model based on one or more correlations between the one or more water conditions and the supplemental data;
determining a predicted water condition based on the water condition model and the one or more water conditions; and
transmitting an alert to one or more devices based on determining that the predicted water condition indicates a predicted contaminant level above a threshold.

9. The system of claim 8, wherein the computer readable instructions are configured to control the one or more processors to perform operations comprising:
monitoring a water sensor network comprising a plurality of water sensors at one or more known locations; and
tracking variations in the one or more water conditions with respect to the one or more known locations.

10. The system of claim 9, wherein the water sensor network is distributed between a plurality of public and private water distribution locations.

11. The system of claim 9, wherein the water sensor network is associated with one or more wells accessing an aquifer.

12. The system of claim 9, wherein the computer readable instructions are configured to control the one or more processors to perform operations comprising:
identifying a probable location of introduction of a contaminant based on a rate of change of the one or more water conditions relative to the known locations of the water sensors; and
generating a notification of the probable location and the one or more water conditions.

13. The system of claim 8, wherein the computer readable instructions are configured to control the one or more processors to perform operations comprising:
applying machine learning to train the water condition model to dynamically determine one or more characteristics associated with the one or more water conditions.

14. The system of claim 8, wherein the computer readable instructions are configured to control the one or more processors to perform operations comprising:
accessing forecast data comprising one or more of weather forecast data and environmental forecast data; and
predicting the water condition based on the water condition model and the forecast data.

15. A computer program product comprising a non-transitory computer readable storage medium having program instructions embodied therewith, the program instructions executable by one or more processors to cause the one or more processors to perform operations comprising:
monitoring at least one water sensor to establish a baseline of a water condition model;
monitoring one or more water conditions;
accessing supplemental data comprising one or more of a weather data source and an environmental data source;
applying machine learning to train the water condition model based on one or more correlations between the one or more water conditions and the supplemental data;
determining a predicted water condition based on the water condition model and the one or more water conditions; and
transmitting an alert to one or more devices based on determining that the predicted water condition indicates a predicted contaminant level above a threshold.

16. The computer program product of claim 15, wherein the program instructions control the one or more processors to perform operations comprising:
monitoring a water sensor network comprising a plurality of water sensors at one or more known locations; and
tracking variations in the one or more water conditions with respect to the one or more known locations.

17. The computer program product of claim 16, wherein the program instructions control the one or more processors to perform operations comprising:
identifying a probable location of introduction of a contaminant based on a rate of change of the one or more water conditions relative to the known locations of the water sensors; and
generating a notification of the probable location and the one or more water conditions.

18. The computer program product of claim 15, wherein the program instructions control the one or more processors to perform operations comprising:
applying machine learning to train the water condition model to dynamically determine one or more characteristics associated with the one or more water conditions.

19. The computer program product of claim 15, wherein the program instructions control the one or more processors to perform operations comprising:
accessing forecast data comprising one or more of weather forecast data and environmental forecast data; and
predicting the water condition based on the water condition model and the forecast data.

* * * * *